United States Patent [19]

Anderson

[11] 4,396,023

[45] Aug. 2, 1983

[54] APPARATUS FOR OBTAINING BLOOD SAMPLES FROM ANIMALS SUCH AS MICE OR RATS

[76] Inventor: Porter W. Anderson, 313 Sawyer St., Rochester, N.Y. 14619

[21] Appl. No.: 304,217

[22] Filed: Sep. 21, 1981

[51] Int. Cl.³ .............................................. A61B 5/14
[52] U.S. Cl. ..................................... 128/760; 604/73; 604/317
[58] Field of Search ............... 128/760, 762, 763, 765, 128/276, 278, 280, 281, 282, 299, 300, 301, 302, 23, 32; 604/74, 73, 317

[56] References Cited

U.S. PATENT DOCUMENTS

| | | | |
|---|---|---|---|
| 1,152,818 | 9/1915 | Kells | 128/276 |
| 1,823,544 | 9/1931 | Howe | 128/278 |
| 1,847,658 | 3/1932 | Lasker | 128/281 |
| 1,855,658 | 4/1932 | Whipple et al. | 128/276 |
| 1,861,121 | 5/1932 | Kapsenberg | 128/276 |
| 2,020,252 | 11/1935 | Utterback et al. | 128/276 |
| 2,174,295 | 9/1939 | Trafford | 128/276 |
| 3,032,037 | 5/1962 | Huber | 128/276 |
| 3,815,579 | 6/1974 | Rose | 128/760 |

FOREIGN PATENT DOCUMENTS

| | | | |
|---|---|---|---|
| 595476 | 10/1925 | France | 128/296 |
| 20358 | of 1905 | United Kingdom | 128/300 |

*Primary Examiner*—Kyle L. Howell
*Assistant Examiner*—Harry J. Macey
*Attorney, Agent, or Firm*—Martin Lukacher

[57] ABSTRACT

Blood samples are obtained from the tails of animals such as mice or rats by a disposable tube located in a stopper and disposed in a vacuum flask. The tube is of such length that the tail extends into a receptacle at the end of the tube in which the samples are collected. Vacuum is communicated into the interior of the tube via a hole therein and promotes the flow of blood from the tail. The posterior of the animal makes a vacuum tight seal with the top of the tube on which the animal is seated. The tube is disposable after a single use.

6 Claims, 4 Drawing Figures

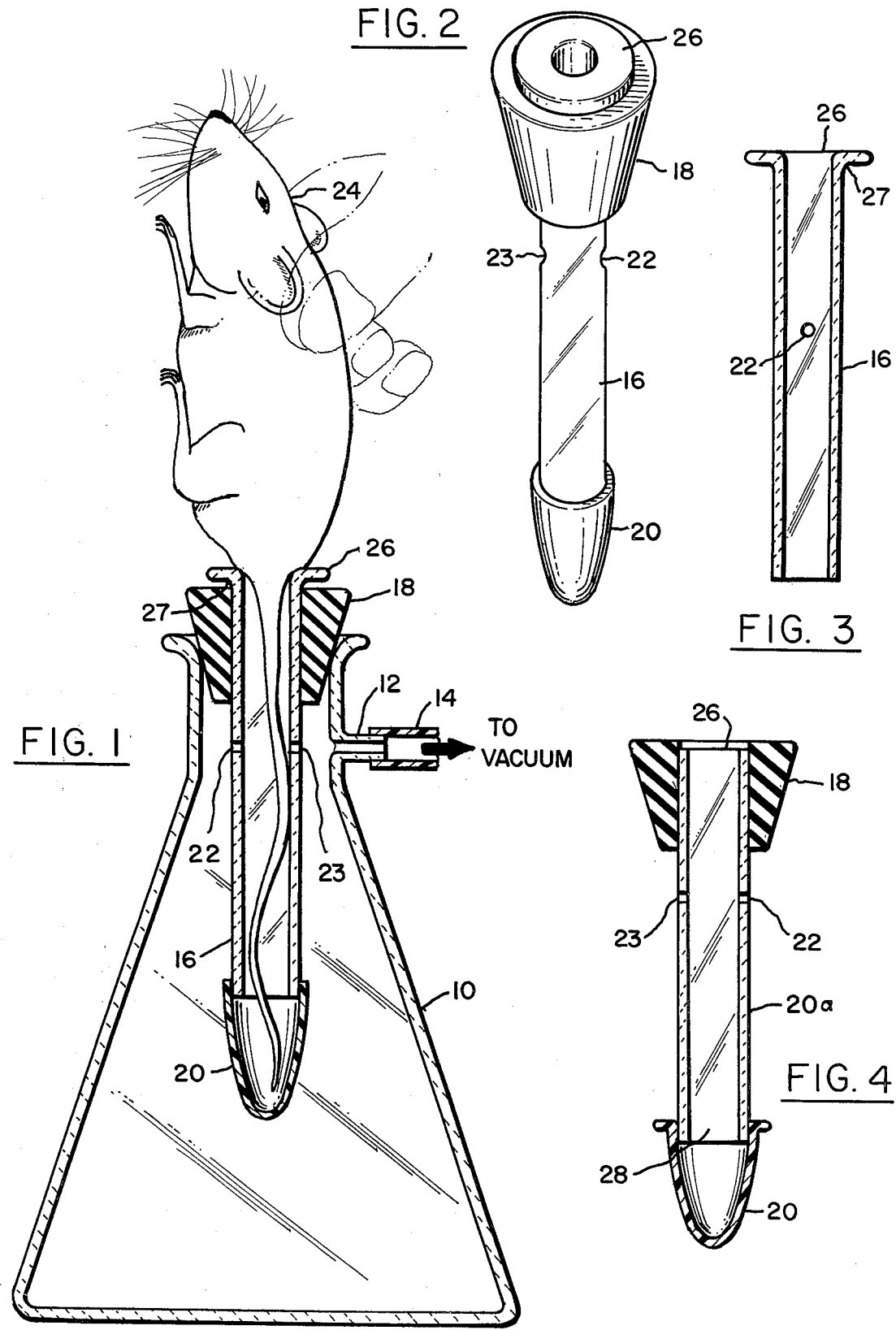

APPARATUS FOR OBTAINING BLOOD SAMPLES FROM ANIMALS SUCH AS MICE OR RATS

DESCRIPTION

The invention relates to apparatus for obtaining blood samples from small, long-tailed mammals, such as mice or rats, conveniently and without destroying the animal.

The invention is especially for use in biomedical laboratories where blood samples from animals, such as mice and rats are used in biomedical studies, for example, in the field of immunology.

Obtaining blood samples from a live mouse or rat has been a difficult procedure. In one method, considered cruel and crude, a pipet is inserted into the eye socket of the animal. In another, blood is permitted to drop into a collection tube from a cut in the animal's tail; in this approach the slow flow and likelihood of clotting make it difficult to collect useful volumes in reasonable time.

Accordingly, it is an object of the present invention to provide improved apparatus for obtaining blood samples from animals, such as mice or rats, conveniently and rapidly.

It is a further object of the present invention to provide improved apparatus which may readily be used by unskilled personnel for obtaining blood samples from small, long-tailed mammals with less chance of serious injury to or destruction of the animal.

It is a still further object of the present invention to provide improved apparatus for obtaining blood samples from small, long-tailed mammals, such as mice or rats, which is inexpensive to manufacture and may be disposable after use.

Briefly described, apparatus in accordance with the invention makes use of a vacuum flask and a one-hole rubber stopper. A tube, which is preferrably flange-topped, is inserted into the stopper which holds the tube in the flask. A blood-receiving receptacle is located at the lower end of the tube in the flask. A hole in the tube provides communication of the vacuum in the flask to the interior of the tube and the receptacle thereof. The animal is seated (on the flange when the tube has a flange) and its tail extends through the tube into the receptacle. The vacuum promotes the flow of blood from the tail which, prior to insertion, has been nicked or transsected. When the desired volume of blood has been collected, the vacuum is turned off and the animal removed. The blood samples are obtained conveniently and without damaging the animal seriously. The receptacle, when not an integral part of the tube, may be sealed and used to transport the blood samples for further processing and tests. The tube, which has become contaminated with blood, may be discarded.

The foregoing and other objects, features and advantages of the invention will become more apparent from a reading of the following description in connection with the accompanying drawings in which:

FIG. 1 is a sectional view showing apparatus for obtaining blood samples in accordance with an embodiment of the invention, while it is being used;

FIG. 2 is a perspective view of the stopper, tube and receptacle of the apparatus shown in FIG. 1;

FIG. 3 is an enlarged, sectional view of a preferred form of flanged top tube; and FIG. 4 is a sectional view showing another embodiment of the tube, stopper and receptacle which is provided in accordance with the invention.

Referring first to FIGS. 1 to 3 there is shown a vacuum flask 10 with a side-arm 12 connected by a tube 14 to a vacuum source.

A tube 16 which may be of glass or plastic, for example, polypropylene, is disposed in one end in a stopper 18. A receptacle 20, such as a disposable polypropylene centrifuge tube is disposed on the lower end of the tube 16. The tube has at least one opening (two aligned openings 22 and 23 being shown) which provides communication between the interior of the tube and the receptacle 20 with the flask 10. Accordingly, the receptacle and the interior of the tube is at vacuum. A low vacuum, such as is generally available in laboratories may be used. The tube 16 has a flange 26 at its top. A radius 27 between the flange and tube wall insures that the flange 26 will come to rest slightly above the top of the stopper 18, thereby enabling the stopper 18 and tube 16 to be separated easily.

In operation, the tube 16 is inserted into the stopper and the receptacle 20 is located at the lower end of the tube. The stopper, tube and receptacle assembly is inserted into the flask. The mouse or rat 24 is held by the dorsal skinfold and its tail is immersed in warm water to cause vasodilation. The tail is wiped dry and its tip nicked or transsected. With the vacuum on, the tail is inserted into the upper end of the tube until the posterior of the mouse or rat engages the upper end of the tube and the stopper 18 so as to make a vacuum seal. It should be noted that the dimensions of the tube and its flange should be just large enough to seat the posterior of the animal. The tubes can be in smaller and larger sizes (diameter) for mice and for rats. For a mouse, the length may be 8 cm., the tube ID 6 mm and OD 8.5 mm. The flange diameter may be 30 mm. The small ID reduces the possibility of sample contamination by hair, feces and urine.

The reduced pressure in the interior of the tube and receptacle promotes and causes an enhanced flow of blood. It will be noted that the tube is of such length that the tail extends somewhat beyond the lower end thereof and into the receptacle 20. When the desired volume of blood has been collected, the vacuum is turned off. Blood flow generally stops and the mouse or rat may be lifted off the stopper 18 and returned to its cage.

The receptacle 20 is removed from the tube 16 and the tube which has been contaminated with blood is discarded.

The receptacle may be used for further processing and tests on the blood sample collected therein. The tube and receptacle may, although it is not preferred, be integral so that the entire tube and receptacle can be used for carrying the blood sample for further processing.

Referring to FIG. 4, there is shown a stopper 18. The tube 20A does not have the flange 26 at the upper end thereof, and with its rim is seated at or below the top of the stopper 18. This stopper is then the surface for the posterior of the animal 24 and the stopper may be contaminated with blood, feces, or urine and must be washed after each use. The tube also has openings 22 and 23 which provide communication for the vacuum to the interior of the flask. The receptacle 20 is attached to the lower end 28 of the tube. The tube may be closed at its lower end so as to provide the receptacle.

The tubes 16 and 20A may have length markings thereon so as to facilitate trimming a section off the bottom of the tube depending upon the length of the animal's tail so that the nicked tip of the tail protrudes into the receptacle.

From the foregoing description it will be apparent that there has been provided improved apparatus for obtaining blood samples from animals having tails, particularly from mice or rats. Variations and modifications in the herein described apparatus, within the scope of the invention, will undoubtedly suggest themselves to those skilled in the art. Accordingly, the foregoing description should be taken as illustrative and not in a limiting sense.

I claim:

1. Apparatus for obtaining blood samples from rodents or small animals, such as mice and rats, having tails extending from the posterior thereof comprising a flask, a stopper, a tube having a blood receptacle at one end thereof, said tube and receptacle having a length approximately equal to that of the tail of the animal and an inside diameter slightly larger than the largest diameter of the tail for receiving said tail, said tube being disposed in said stopper at the end thereof opposite to said one end for seating the posterior of said animal in vacuum tight relationship when said stopper and tube are inserted into said flask, means providing communication for vacuum pressure between the interior of said tube and said flask to promote the flow of blood from said tail into said receptacle.

2. The invention as set forth in claim 1 wherein said receptacle is separable from said tube and is attached thereto for collecting the blood samples.

3. The invention as set forth in claim 1 wherein said tube has a flange at said opposite end thereof, said flange being seated on said stopper for providing said vacuum seal with the posterior of the animal.

4. The invention as set forth in claim 3 wherein said tube has a radius between said flange and the outer surface of said tube which provides for clearance between said stopper and said flange for ease of separation thereof.

5. The invention as set forth in claim 1 wherein said tube consists either of glass or plastic.

6. The invention as set forth in claim 5 wherein said tube consists of polypropylene plastic.

* * * * *